(12) United States Patent
Boyd et al.

(10) Patent No.: US 7,806,914 B2
(45) Date of Patent: Oct. 5, 2010

(54) DYNAMIC SPINAL STABILIZATION SYSTEM

(75) Inventors: Lawrence M. Boyd, Durham, NC (US); Tyler P. Lipschultz, New Canaan, CT (US); Mark D. LoGuidice, Southport, CT (US); Andrew Carter, Acton, MA (US)

(73) Assignee: Spine Wave, Inc., Shelton, CT (US)

( * ) Notice: Subject to any disclaimer, the term of this patent is extended or adjusted under 35 U.S.C. 154(b) by 1736 days.

(21) Appl. No.: 10/749,640

(22) Filed: Dec. 31, 2003

(65) Prior Publication Data
US 2005/0143823 A1 Jun. 30, 2005

(51) Int. Cl.
*A61B 17/88* (2006.01)
(52) U.S. Cl. .................. 606/279; 606/257; 606/314
(58) Field of Classification Search .................. 606/73, 606/314, 257, 279; 623/17.12–17.16
See application file for complete search history.

(56) References Cited

U.S. PATENT DOCUMENTS

| | | | |
|---|---|---|---|
| 4,645,453 A | 2/1987 | Niznick | |
| 4,743,260 A | 5/1988 | Burton | |
| 4,805,602 A | 2/1989 | Puno et al. | |
| 4,836,196 A | 6/1989 | Park et al. | |
| 4,946,458 A | 8/1990 | Harms et al. | |
| 5,002,542 A | 3/1991 | Frigg | |
| 5,011,484 A | 4/1991 | Breard | |
| 5,041,113 A | 8/1991 | Biedermann et al. | |
| 5,042,982 A | 8/1991 | Harms et al. | |
| 5,092,866 A | 3/1992 | Bread et al. | |
| 5,167,664 A | 12/1992 | Hodorek | |
| 5,180,393 A | 1/1993 | Commarmond | |
| 5,207,678 A | 5/1993 | Harms et al. | |

(Continued)

FOREIGN PATENT DOCUMENTS

EP   0 381 588 B2   3/2000

(Continued)

OTHER PUBLICATIONS

Mulholland, Robert C. and Sengupta, Dilip K., "Rational, Principles and Experimental Evaluation of the Concept of Soft Stabilization", EUR Spine J (2002) 11 (Suppl.2): S198-S205, © Springer-Verlag 2002, (8 pages).

(Continued)

*Primary Examiner*—Eduardo C Robert
*Assistant Examiner*—Julianna N Harvey
(74) *Attorney, Agent, or Firm*—Maginot, Moore & Beck, LLP

(57) ABSTRACT

A dynamic stabilization construct for implantation within the spine comprises bone anchors that include a flexible portion between the bone engaging and head portions of the anchor. The head portion is configured to mate with different types of stabilization elements adapted to span between spinal motion segments. The engagement portion can also be configured for different types of fixation to a motion segment, such as within the pedicle of a vertebra. The flexible portion permits limited bending of the bone anchor beneath the level of the stabilization element. In one embodiment, the flexible portion is integrated into the body of the bone anchor in the form of hinge elements. In another embodiment, a separate flexible element, such as a spacer or spring, is interposed between the head and engagement portions. In a further embodiment, the bone anchor includes a portion having a reduced cross-section. The flexible bone anchors may be used to tailor the dynamic flexibility of spinal stabilization instrumentation at each level of the construct.

12 Claims, 6 Drawing Sheets

U.S. PATENT DOCUMENTS

| | | | |
|---|---|---|---|
| 5,209,751 A | 5/1993 | Farris et al. | |
| 5,219,349 A | 6/1993 | Krag et al. | |
| 5,242,446 A | 9/1993 | Steffee et al. | |
| 5,261,912 A | 11/1993 | Frigg | |
| 5,344,422 A | 9/1994 | Frigg | |
| 5,363,841 A | 11/1994 | Coker | |
| 5,486,174 A | 1/1996 | Fournet-Fayard et al. | |
| 5,501,684 A | 3/1996 | Schlapfer et al. | |
| 5,534,028 A * | 7/1996 | Bao et al. | 623/17.16 |
| 5,540,688 A | 7/1996 | Navas | |
| 5,545,163 A | 8/1996 | Miller et al. | |
| 5,562,737 A | 10/1996 | Graf | |
| 5,569,248 A | 10/1996 | Mathews | |
| 5,591,165 A | 1/1997 | Jackson | |
| 5,616,143 A | 4/1997 | Schlapfer et al. | |
| 5,628,740 A | 5/1997 | Mullane | |
| 5,672,175 A | 9/1997 | Martin | |
| 5,707,372 A | 1/1998 | Errico et al. | |
| 5,782,831 A | 7/1998 | Sherman et al. | |
| 5,961,516 A | 10/1999 | Graf | |
| 6,004,323 A | 12/1999 | Park et al. | |
| 6,010,507 A | 1/2000 | Rudloff | |
| 6,015,409 A | 1/2000 | Jackson | |
| 6,017,345 A | 1/2000 | Richelsoph | |
| 6,083,229 A | 7/2000 | Constantz et al. | |
| 6,086,590 A | 7/2000 | Margulies et al. | |
| 6,123,706 A | 9/2000 | Lange | |
| 6,132,464 A * | 10/2000 | Martin | 623/17.15 |
| 6,149,655 A | 11/2000 | Constantz et al. | |
| 6,179,838 B1 | 1/2001 | Fiz | |
| 6,206,882 B1 | 3/2001 | Cohen | |
| 6,214,004 B1 | 4/2001 | Coker | |
| 6,224,597 B1 | 5/2001 | Coker | |
| 6,241,730 B1 | 6/2001 | Alby | 606/61 |
| 6,293,949 B1 * | 9/2001 | Justis et al. | 606/279 |
| 6,375,682 B1 * | 4/2002 | Fleischmann et al. | 623/17.12 |
| 6,391,030 B1 | 5/2002 | Wagner et al. | |
| 6,402,750 B1 | 6/2002 | Atkinson et al. | |
| 6,432,109 B1 | 8/2002 | Letendart et al. | |
| 6,514,255 B1 | 2/2003 | Ferree | |
| 6,551,320 B2 | 4/2003 | Lieberman | |
| 6,558,387 B2 | 5/2003 | Errico et al. | |
| 6,575,975 B2 | 6/2003 | Brace et al. | |
| 6,582,431 B1 | 6/2003 | Ray | |
| 6,610,091 B1 * | 8/2003 | Reiley | 623/17.11 |
| 6,613,050 B1 | 9/2003 | Wagner et al. | |
| 6,616,669 B2 | 9/2003 | Ogilvie et al. | |
| 6,626,944 B1 | 9/2003 | Taylor | |
| 6,986,771 B2 | 1/2006 | Paul et al. | |
| 6,989,011 B2 | 1/2006 | Paul et al. | |
| 2001/0037111 A1 * | 11/2001 | Dixon et al. | 606/61 |
| 2002/0019637 A1 | 2/2002 | Frey et al. | |
| 2002/0068937 A1 | 6/2002 | Kuntz | |
| 2002/0072800 A1 * | 6/2002 | Goble et al. | 623/17.11 |
| 2002/0103487 A1 | 8/2002 | Errico et al. | |
| 2002/0138077 A1 | 9/2002 | Ferree | |
| 2002/0143329 A1 * | 10/2002 | Serhan et al. | 606/61 |
| 2002/0165550 A1 | 11/2002 | Frey et al. | |
| 2002/0183745 A1 | 12/2002 | Kuntz | |
| 2002/0198527 A1 * | 12/2002 | Muckter | 606/73 |
| 2003/0004511 A1 | 1/2003 | Ferree | |
| 2003/0028196 A1 | 2/2003 | Bonutti | |
| 2003/0055427 A1 | 3/2003 | Graf | |
| 2003/0065329 A1 | 4/2003 | Vaughan | |
| 2003/0083657 A1 * | 5/2003 | Drewry et al. | 606/61 |
| 2003/0220643 A1 * | 11/2003 | Ferree | 606/61 |
| 2005/0033434 A1 | 2/2005 | Berry | |
| 2005/0113927 A1 | 5/2005 | Malek | |
| 2005/0154390 A1 * | 7/2005 | Biedermann et al. | 606/61 |

FOREIGN PATENT DOCUMENTS

| | | |
|---|---|---|
| WO | WO 01/45576 | 6/2001 |
| WO | WO 02/24087 | 3/2002 |
| WO | WO 02/102259 | 12/2002 |

OTHER PUBLICATIONS

Sénégas, J., "Mechanical Supplementation by Non-Rigid Fixation in Degenerative Intervertebral Lumbar Segments: The Wallis System", Eur Spine J (2002) 11 ((Suppl. 2): S164-S169, © Springer-Verlag 2002, (6 pages).

Dunsker, Stewart B., Schmidek, Henry H., Frymoyer, John, and Kahn, Alfred, The Unstable Spine (Thoracic, Lumbar, and Sacral Regions), Grune & Stratton, Inc. 1986, (19 pages).

"Modulus System™: Fusion, Stabilization, or Augmentation", MEKANIKA: The Spinal Stabilization Company, http://www.mekanika.com/htm/modsystem.htm, Nov. 15, 2003, (4 pages).

Seifert, Jeffrey L., Sairyo, Koichi, Goel, Vijay K., Grobler, Leon J., Groslan, Nicole M., Spratt, Kevin F., and Chesmel, Kathleen D., "Stability Analysis of an Enhanced Load Sharing Posterior Fixation Device and Its Equivalent Conventional Device in a Calf Spine Model", Spine, vol. 24, No. 21, pp. 2206-2213, © Lippincott, Williams & Wilkins, Inc. (8 pages).

Swanson, Kyle E., Lindsey, Derek P., Hsu, Ken Y., Zucherman, James F. and Yerby, Scott A., "The Effect of Interspinous Implant on Intervertebral Disc Pressures", Spine, vol. 28, No. 1, pp. 26-32, © Lippincott, Williams & Wilkins, Inc., (9 pages).

Garner, Matthew D., Wolfe, Steven J., Kuslich, Stephen D., "Development and Preclinical Testing of a New Tension-Band Device for the Spine: The Loop System", Eur Spine J (2000) 11 (Suppl. 2): S186-191, (6 pages).

"The Concept of "Flexible Stabilization" (Dynamic Spine Stabilization)", The Burton Report©, file://C:\Windows\TEMP|triDIMLM.htm, Apr. 29, 2003, (3 pages).

"Wallis", Spine Next, Evoluer Autrement, http://www.spinenext.com, (1 pages).

Senegas, Jacques, "Senegas System: Concept of Posterior Stabilisation: Mechanical Supplementation by Dynaminc Fixation in Degenerative Intertebral Lumbar Segments: The Wallis System", (2 pages).

Suzuki, Kane, Mochida, Joji, Chiba, Masahiro and Kikugawa, Hisao, "Posterior Stabilization of Degenerative Lumbar Spondylolisthesis with a Leeds-Keio Artificial Ligament: A Biomechanical Analysis in a Porcine Vertebral Model", (10 pages).

Mochida, Joji, Suzuki, Kane, Chiba, Masahiro, "How to Stablize a Single Level Lesion of Degenerative Lumbar Spondylolisthesis", Clinical Orthopaedics and Related Research, No. 368, pp. 126-134, © Lippincott, Williams & Wilkins, Inc., (9 pages).

Taylor, Jean, "Minimal Access for Interspinous Stabilisation", (6 pages).

Caserta, S., La Maida, G.A., Misaggi, B., Peroni, D., Pietrabissa, R., Raimondi, M.T., Redaelli, A., "Elastic Stabilization Alone or Combined with Rigid Fusion in Spinal Surgery: A Biomechanical Study and Clinical Experience based on 82 cases", Eur Spine J (2002) 11(Suppl.2):S192-S197, © Springer-Verlag 2002, (6 pages).

Hadlow, Simon, Fagan, Andrew, Terrence, Hillier and Fraser, Robert, "The Graf Ligamentoplasty Procedure: Comparison with Posterolateral Fusion in the Management of Low Back Pain", http://gateway2.ovid.com/ovidweb.cgi, May 20, 2003, (14 pages).

Konno, Shinichi and Kikuchi, Shinichi, "Prospective Study of Surgical Treatment of Degenerative Spondylolisthesis: Comparison Between Decompression Alone and Decompression with Graf System Stabilization", Spin, vol. 25 (12), Jun. 15, 2000, (10 pages).

Gardner, Alan and Pande Ketan, Graf Ligamentoplasty: A 7-Year Follow-Up, Eur Spine J (2002) 11 (Suppl.2): S157-S163, © Springer-Verlag 2002, (7 pages).

Nydegger, T. and Dubois, G., "Dynamic Neutralisation System for the Spine: Biomechanical Aspects", (1 page).

Eberlein, Robert, Holzapfel, Christian A, and Schulze-Bauer, A.J., "Assessment of a Spinal Implant by Means of Advanced FE Modeling of Intact Human Intervertebral Discs", WCCM V Jul. 7-12, 2002, (14 pages).

Stoll, Thomas M., Dubois, Giles, Schwarzenbach, Othmar, "The Dynamic Neutralization System for the Spine: A Multi-Center Study of a Novel Non-Fusion System", European Spine Journal, http://link.springer-ny.com/link/service/journals/00586/contents/02/00438/paper//s00586-002, (18 pages).

Freudiger, S., Dubois, G. and Lorrain, M., "Dynamic Neutralisation of the Lumbar Spine Confirmed on a New Lumbar Spine Simulator in Vitro", Arch Orthop Trauma Surg (1999): 119:127-132, © Springer-Verlag-1999, (6 pages).

Rauchnung, Wolfgang, "Design Rational and Implantation of Dynesis", (2 pages).

Centerpulse, Centerpulse Spine-Tech, http://www.centerpulse.com/centerpulse/Investors/NewsQuotes/?view=6340, Apr. 29, 2003, (2 pages).

Sengupta, Dilip K., Mulholland, Robert C., Herkowitz, Harry N., Hochschuler, Stephen H., "Loads Sharing Characteristics of Two Novel Soft Stabilization Devices in the Lumbar Motion Segments: A Biomechanical Study in Cadaver Spine", date unknown, (3 pages).

X-Stop IPD System, product brochure—Kyphon, Inc., 2007.

* cited by examiner

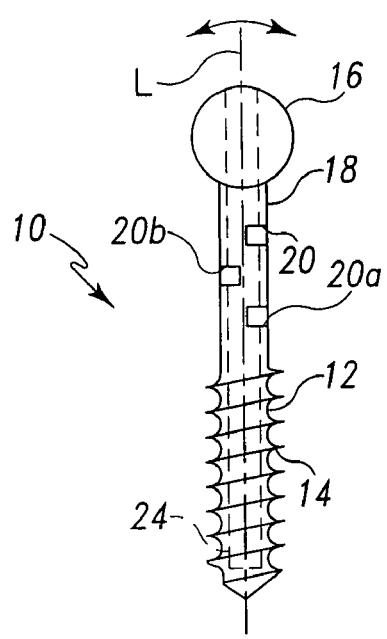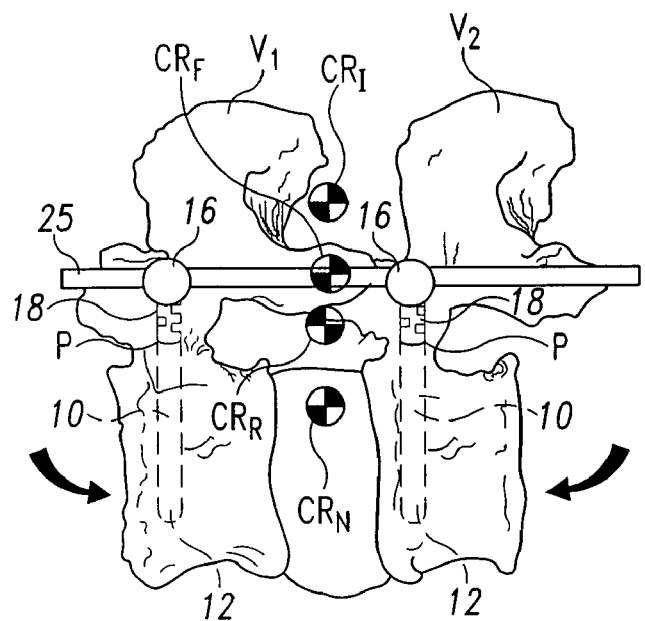
Fig. 1
Fig. 3
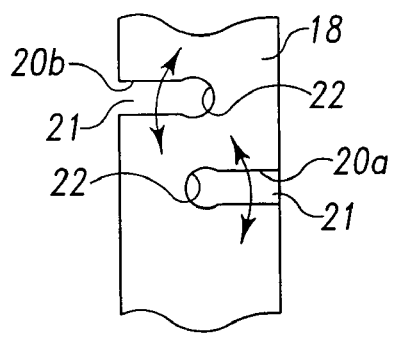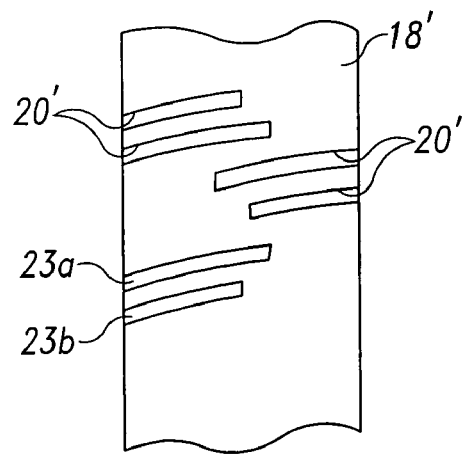
Fig. 2A
Fig. 2B

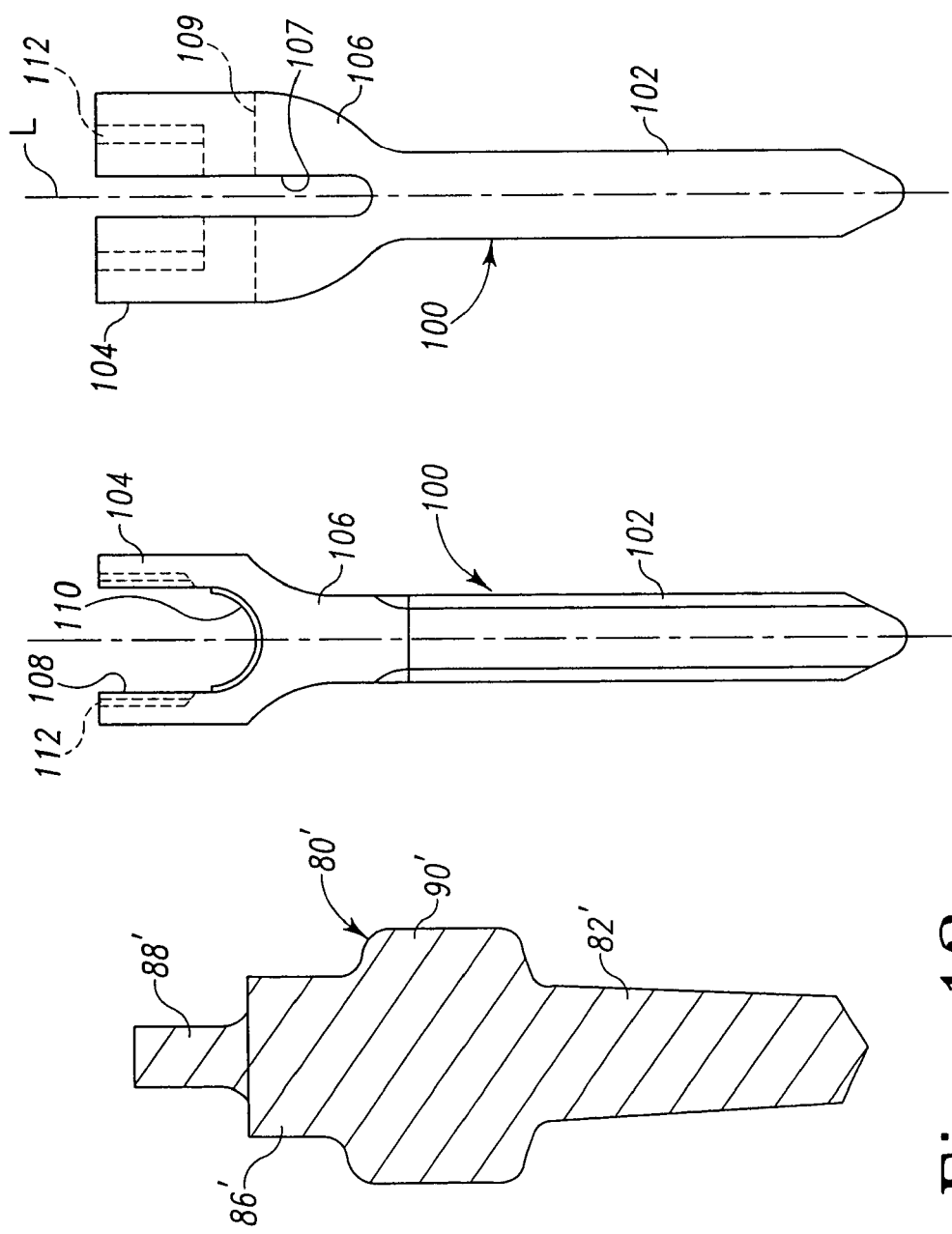

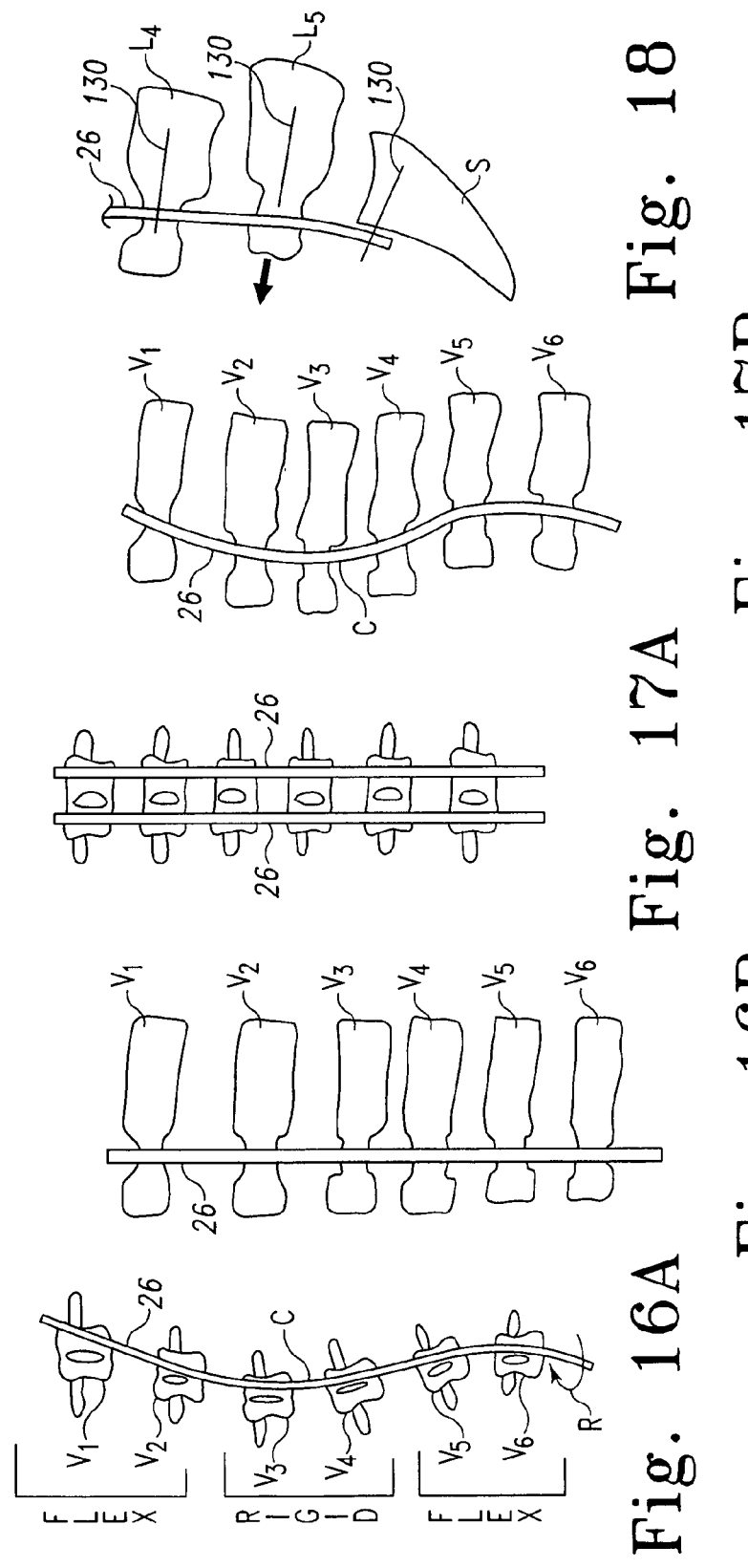

DYNAMIC SPINAL STABILIZATION SYSTEM

The present invention relates to spinal implant systems, and particularly systems for stabilization of the spine. The invention provides a dynamic stabilization system that permits limited relative movement between the instrumented vertebrae and the stabilization system.

In the past, the principal protocol for the treatment of the spine has been rigid fixation combined with fusion of the affected vertebral body or intervertebral disc. Arthrodesis, as this approach is known, has been achieved with a variety of rigid fixation elements, such as spinal rods or plates that are rigidly fixed to a vertebra using bone screws, bone bolts and spinal hooks. However, spinal fusion has been recognized to have limitations in the treatment of disc degeneration, especially in the earlier stages of the degeneration where it may be unnecessary to eliminate motion of the spinal motion segments.

Clinical studies suggest that cells of the intervertebral disc respond favorably to reduced (but not eliminated) mechanical loading through deposition of extracellular matrix proteins (collagen, proteoglycan, fibronectin, etc.) into the disc space. In some cases, a degenerated disc may simply involve a mechanically overloaded and hypermobile segment that can be repaired by reversing the mechanically damaging load environment. For instance, clinical experiences with dynamic stabilization systems suggest that the disc becomes increasingly hydrated over time, as judged by MRI scanning.

Spinal instability is a recognized effect of degenerative disc disease. In contrast to arthrodesis, arthroplasty is a protocol that contemplates restoring segmental spinal motion while treating the degenerative condition. Arthroplasty has been successfully used in the treatment of degenerative conditions of the hip and knee. In recent years, efforts have been made to implement arthroplasty in the spine, and most particularly in the intervertebral space. Intradiscal arthroplasty is now clinically available in the form of articulating prosthetic discs and polymeric disc nucleus replacements. With the availability of viable intradiscal arthroplasty devices, interest has grown in providing some means for dynamic spinal stabilization—i.e., stabilization that still permits some degree of mobility between spinal segments.

Drawing from the approaches developed for intradiscal arthroplasty, efforts have made to develop an extradiscal arthroplasty. These systems offer the advantage of "soft stabilization" that limit, rather than eliminate, spinal segment motion. Current theories suggest that preventing movement of the spinal segments may not be a significant factor in clinical success of spinal stabilization systems. Instead, these theories focus on creating a normal loading pattern for the spine as a primary vehicle for successful spinal instrumentation. Thus, the goals for dynamic stabilization has been to restrict movement of the spine to a zone or range where normal or near normal loading of the spinal segments can occur. At the same time, dynamic stabilization techniques have sought to prevent the spine from adopting a position or orientation where abnormal loading of the spine can occur.

One approach to achieve these goals for dynamic stabilization utilizes the spinous process. Thus, in one system, flexible "ligaments" are engaged around the spinous process of adjacent vertebrae. Another form of flexible "ligament" is attached to the spinous process by way of small screws. In yet another approach, a polymeric spacer is held in place between the adjacent spinous processes. One system utilizes a coil spring that spans several vertebrae and that is anchored to the lamina of the end vertebrae. In one version, a rod extends through part of the coil spring to control rotation.

Some dynamic stabilization systems have relied upon fixation to the pedicle of the vertebrae. In these types of systems, a pedicle screw is threaded into the pedicle of adjacent vertebrae. A member spans between the heads of the pedicle screws to limit the movement of the spinal segments. In one device, known as the Graf Ligament, a non-elastic band is wrapped around pedicle screw anchors. The non-elastic bands lock the spinal segment into lordosis, while permitting minimal rotation movements of the spine.

Another system utilizing pedicle screws, known as the Dynesys System, incorporates a polymeric cylinder between the bone anchors. The Dynesys System permits, but limits, relative motion between adjacent vertebrae. The FASS System essentially integrates features from the Graf and Dynesis systems.

The DSS System employs still another approach by including a spring element connected to pedicle screws. The spring element is contained within a polyurethane tube to prevent tissue ingrowth. Finally, some systems utilize a rigid member, such as a spinal plate, spanning between vertebrae. The flexible stabilization feature is incorporated into the interface between the pedicle screw and the rigid member, such as through a flexible washer or a spherical screw-plate interface.

These prior extradiscal arthroplasty approaches all involve the introduction of flexible elements between spinal motion segments. Consequently, many of these systems are susceptible to over-loading the disc annulus or are, by necessity, unduly restrictive with respect to motion of the spinal segment.

Moreover, these prior systems are not capable of altering the stiffness of a segment in various loading modes (e.g., flexion/extension, compression, lateral bending and axial rotation). Furthermore, these early approaches to arthrodesis do not allow selection of where, or at which motion segment, dynamic movement is permitted. Finally, no system exists that can readily convert to and from a soft stabilization to a more rigid or completely rigid system.

SUMMARY OF THE INVENTION

In order to address some of the difficulties associated with prior dynamic stabilization systems, the present invention contemplates a novel bone anchor for use in the stabilization of motion segments of the spine. In a preferred embodiment, the bone anchor comprises an engagement portion configured for engagement within a spinal motion segment and a head portion configured for engagement to a stabilization element outside the vertebral body. The engagement portion can be of many known forms, such as bone screw, bone bolt or spinal hook. The head portion can also assume a variety of known configurations depending upon the type of stabilization element being utilized for the construct. For instance, the stabilization element can be a spinal rod or an elongated plate. The head portion can be configured to engage either type of stabilization element.

In an important feature of this embodiment of the invention, the bone anchor further comprises a flexible portion between the shank and the head portion. The flexible portion permits movement of the head portion relative to the engagement portion when both portions are fixed to the stabilization element and the vertebral body, respectively. In certain embodiments, the flexible portion is arranged to reside substantially extra-pedicular when the bone anchor is engaged within the pedicle of a vertebra. The flexible portion is configured to limit the relative movement between the head portion and the engagement portion to a single plane, most typically a plane parallel to the sagittal plane through the spine.

In one embodiment, the flexible portion includes an elongated body spanning between the engagement portion and the head portion. The elongated body defines at least one hinge element, and preferably several such hinge elements. The hinge element includes a slot defined in the elongated body having an axis substantially transverse to the longitudinal axis of the body. Several hinge elements can be arranged in alternating opposing relation along the length of the body. To reduce stress risers, each slot terminates within the elongated body with a bore substantially perpendicular to the axis of the slot.

In an alternative embodiment, the flexible portion includes a helical spring disposed between the engagement portion and the head portion. The spring can be constrained to deflect in a predetermined plane or planes.

In a further embodiment, the flexible portion includes an elongated flexible element disposed between the engagement portion and the head portion. The flexible element is a flexible sleeve or a similar tube-like structure spanning between the head and engagement portions. In one configuration, the engagement portion includes an elongated shank, and the elongated shank and the flexible sleeve have substantially equal outer diameters. Moreover, the elongated shank and the flexible sleeve can be configured for interlocking engagement.

The flexible sleeve may be affixed to the head and engagement portions. Alternatively, a tension element may be provided that is anchored at one end to the engagement portion and at an opposite end to the head portion. The tension element extends through the flexible sleeve to clamp the sleeve between the head portion and the engagement portion.

In one embodiment, the tension element is a cable. With this embodiment, the engagement portion includes an elongated shank that defines a longitudinal bore, opening at a proximal and an opposite distal end of the shank. The flexible element and the head portion also define a respective bore therethrough aligned with the longitudinal bore. The cable is then anchored to the shank at the distal end and extends through the longitudinal bore and the bores in the flexible element and the head portion. The cable anchor can be accomplished by the cable including an enlarged head relative to the diameter of the longitudinal bore at the distal end of the shank.

In yet another embodiment of the invention, the bone anchor includes an engagement portion having an elongated shank, in which at least the shank and the flexible portion are integral. The flexible portion defines a cross-sectional area along the longitudinal axis of the shank that is substantially less than the cross-sectional area of the shank along the longitudinal axis. Thus, the flexible portion will exhibit bending tendencies in the region of the reduced cross section. This bone anchor comprises means surrounding the flexible portion for preventing bone overgrowth at the flexible portion.

To achieve the reduced cross sectional area, the flexible portion has a first dimension in a first plane passing through the bone anchor that is less than a dimension of the engagement portion in the first plane. In certain embodiments, the flexible portion has a second dimension in a second plane substantially transverse to the first plane that is greater than the first dimension. With this configuration, the bone anchor exhibits greater flexibility in the first plane than in the second plane. In still other embodiments, the second dimension of the flexible portion is also greater than a dimension of the engagement portion in the second plane.

An alternative embodiment of the inventive bone anchor utilizes a flexible portion that includes an elongated body spanning between the engagement portion and the head portion, in which the elongated body defines an elongated slot therethrough. The slot extends generally parallel to the longitudinal axis of the elongated body in a sort of "clothes pin" configuration. Preferably, the elongated slot originates in the head portion and extends toward the engagement portion.

The present invention further contemplates a dynamic spinal stabilization system comprising a stabilization element configured to span a length of the spine adjacent the vertebrae and at least one bone anchor having a flexible intermediate portion and at least one other anchor selected from the group including a bone anchor having a flexible intermediate portion, a spinal hook having a hook portion configured to engage a portion of a vertebra and a head portion configured to engage the stabilization element, and a substantially rigid bone screw having a threaded portion configured to engage a portion of a vertebra and a head portion configured to engage the stabilization element.

The stabilization element can be an elongated plate defining at least two openings therethrough for receiving a corresponding one of the bone anchors. In this case, the head portion of the bone anchors can include a substantially spherical surface, while the elongated plate can define a substantially spherical recess at each of the openings.

The present invention further contemplates a method for dynamic stabilization of motion segments of the spine comprising the steps of:

1) positioning a stabilization element adjacent the spine, the stabilization element configured to span a length of the spine between at least two motion segments;
2) engaging bone anchors to at least two motion segments; and
3) coupling the bone anchors to the stabilization element, with at least one of the bone anchors coupled to permit deflection of the bone anchor between the stabilization element and the motion segment.

This method may be performed in conjunction with repairing or replacing all or part of the intervertebral disc between at least two motion segments.

Another inventive method dynamic stabilization of motion segments of the spine comprises the steps of:

1) positioning a stabilization element adjacent the spine, the stabilization element configured to span a length of the spine between at least two motion segments;
2) engaging bone anchors to at least two motion segments; and
3) coupling the bone anchors to the stabilization element, with at least one of the bone anchors configured to produce a center of rotation for the motion segment between the stabilization element and the normal anatomic center of rotation for the motion segment.

The present invention contemplates improvements to a method for correction of scoliosis in which a contoured rod is engaged to at least a portion of the deformed spine and is rotated to de-rotate the spine in the transverse plane. In particular, the improvement comprises engaging at least one vertebrae at either or both the superior and inferior ends of the rod to the rod to provide a center of rotation for the at least one vertebra that is between the rod and the normal anatomic center of rotation for the vertebra.

The invention also provides improvements to a method for correction of spondylolisthesis in which a slipped vertebra is pulled posteriorly to a stabilization element engaged to spinal elements adjacent the slipped vertebra. This improvement comprises engaging a bone anchor to the slipped vertebra that is configured to be pulled toward the stabilization element and that is configured to provide a center of rotation for the slipped vertebra that is between the stabilization element and the normal anatomic center of rotation for the vertebra.

It is one object of the invention to provide devices and methods that permit improved dynamic stabilization of the spine. A further object resides in features of the invention that allow tailoring of the flexibility at each instrumented spinal motion segment. Other objects and certain benefits of the invention will be appreciated from the following written description of the preferred embodiments, taken together with the accompanying figures.

DESCRIPTION OF THE FIGURES

FIG. 1 is an elevational view of a bone anchor in accordance with one embodiment of the present invention.

FIGS. 2a-2b are enlarged views of alternative embodiments for the flexible portion for the bone anchor shown in FIG. 1.

FIG. 3 is a side view of a dynamic stabilization system for implantation into a portion of the spine utilizing the bone anchor shown in FIG. 1.

FIG. 12 is a cross-sectional view of the bone anchor shown in FIG. 10, taken along line A-A as viewed in the direction of the arrows.

FIG. 13 is a front view of a bone anchor according to a further embodiment of the invention.

FIG. 14 is a side view of the bone anchor shown in FIG. 13.

FIG. 15 is a front cross-sectional view of a clamp for engaging the head portion of the bone anchor shown in FIGS. 13 and 14.

FIGS. 16a-16b are schematic representations of a scoliotic spine before correction using a rod de-rotation technique, showing the rod from an A/P and a lateral view.

FIGS. 17a-17b are schematic representations of the spine after de-rotation.

FIG. 18 is a lateral schematic representation of a correction for spondylolisthesis.

DESCRIPTION OF THE PREFERRED EMBODIMENTS

Figure 4A:
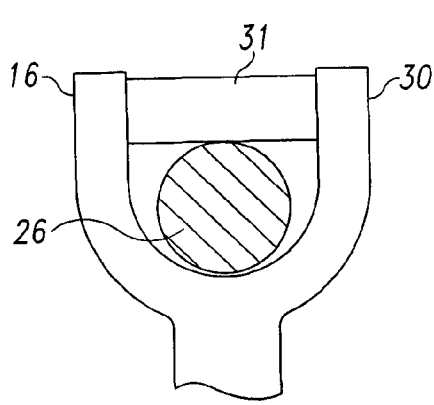
FIGS. 4a-4c are alternative configurations for the head portion of the bone anchor shown in FIG. 1.

While the invention has been illustrated and described in detail in the drawings and foregoing description, the same should be considered as illustrative and not restrictive in character. It is understood that only the preferred embodiments have been presented and that all changes, modifications and further applications that come within the spirit of the invention are desired to be protected.

The present invention contemplates a bone fastener or anchor that is configured to engage a portion of a vertebra and to connect to a stabilization element adapted to span across a spinal motion segment. The bone anchor includes a flexible portion between the vertebra and the stabilization element that permits limited movement of the instrumented vertebrae without commensurate movement of the stabilization element.

In accordance with one embodiment of the invention shown in FIG. 1, a bone anchor 10 is provided that has an engagement portion 12 which may be an elongated shank with external threads 14 configured for engagement within a vertebra. The shank 12 and threads 14 are sized and configured for engagement within any portion of the vertebra, such as the pedicle or vertebral body. Preferably, the threads are configured for anchoring within the cancellous bone of the vertebra.

For the purposes of illustrating the present invention, the bone engagement portion of the anchor has been described as a bone screw or bolt configuration. However, it is understood that other devices for engaging a spinal motion segment or vertebra are contemplated, such as a spinal hook. Moreover, it is understood that the configuration of the elongated shank can be modified, for instance to promote bone ingrowth, or to permit implantation within the intradiscal space.

The anchor 10 includes a head portion 16 that is configured to engage a stabilization member spanning between adjacent vertebrae. As explained in detail herein, the head portion 16 can assume a variety of configurations depending upon the configuration of the stabilization member.

In one feature of the invention, the anchor 10 includes a flexible portion 18 interposed between the head portion 16 and the engagement portion 12. In the embodiment depicted in FIG. 1, this flexible portion 18 includes one or more hinge elements 20. More particularly, in the specific embodiment the hinge elements include elements 20a oriented in one direction relative to the longitudinal axis L of the anchor, and elements 20b in an opposing orientation. These hinge elements 20 represent a region of reduced bending stiffness that permits localized bending about the hinge element. It is thus contemplated that this localized bending will act to open or close the hinge elements, depending upon the direction of movement of the head portion 16 relative to the engagement portion 12, as represented by the curved arrows in FIG. 1.

The number, size and arrangement of the hinge elements 20 may be modified depending upon the amount of bending flexibility that is desired for the particular spinal stabilization. For instance, fewer hinges result in a stiffer bone anchor than a greater number of hinges. In addition, the width of the mouth of the slots will determine the range of bending movement of the flexible portion 18. In other words, a wider hinge element will be capable of a greater angular range of movement than a narrower hinge element.

Two exemplary hinge configurations are shown in FIGS. 2a and 2b. In one specific embodiment shown in FIG. 2a, the hinge elements 20a and 20b are defined by slots 21 cut into the bone anchor perpendicular to its longitudinal axis. Each slot 21 terminates in a bore 22 that is most preferably formed along a circumference of the bone anchor. The bores 22 help limit the occurrence of stress risers at the interior of the slots, and may also improve the bending characteristics of the hinge element 20a, 20b.

In the specific embodiment shown in FIG. 2b, the hinge elements 20' of the flexible portion 18' are in the form of curved slots. Moreover, the elements 20' are aligned at a non-perpendicular angle relative to the longitudinal axis of the anchor. As shown in FIG. 2b, each hinge element 20' is shown with one slot 23a extending past the center of the flexible portion 18' and an adjacent shorter slot 23b. The configuration of FIG. 2b allows the slots 23a, 23b to be thinner in width than the slots 21 of the embodiment in FIG. 2a, while achieving substantially the same degree of bending movement.

Referring to FIG. 3, one form of dynamic stabilization system is shown using the bone anchor 10 shown in FIG. 1. In particular, the engagement portion 12 of two anchors are engaged within adjacent vertebrae $V_1$ and $V_2$. Preferably, the anchors are threaded into the pedicle P of each vertebra. In accordance with the preferred embodiment, the anchors 10 are threaded into the pedicle to a depth where the flexible portions 18 are outside the pedicle so that the anchor can deflect through its full range of angular motion. However, the anchor may be embedded within the vertebra to a depth that encompasses part of the flexible portion 18. It is contemplated in this circumstance that the amount of bending flexibility of the bone anchor 10 may be calibrated by embedding one or more hinge elements, thereby preventing bending of the anchor about that hinge element.

In an alternative embodiment, the bone anchor 10 can include a bore 24, as shown in dashed lines in FIG. 1, which extends along the axis L of the anchor. The bore 24 is configured to receive a stiffening rod (not shown) that can be placed within the bore to essentially convert the anchor into a substantially rigid fastener. The rod can have a length sufficient to fill substantially the entire bore 24, or can have a shorter length. Where the rod has a shorter length, it will traverse less than all of the hinge elements 20. Thus, the rod can prevent deflection of the anchor at the lowermost hinge elements, such as elements 20a, 20b in FIG. 1, while the upper most hinge elements are unencumbered.

As with any spinal implant, fatigue resistance is an important property of the bone anchors of the present invention, such as anchor 10. Thus, the implant can be formed of accepted medical grade materials, such as stainless steel, or other materials, such as polymers, composites or super-elastic alloys, that exhibit sufficient fatigue resistance under normal spinal loading conditions and load cycles. Preferably, the hinge elements 20 are configured to minimize stress concentrations, such as through the use of radiused corners. Furthermore, the material can be strengthened during the manufacturing process, such as by minimizing surface roughness, pre-treating the surface (e.g., Ti nitriding, chroming), or pre-stressing the surface (e.g., by shot-peening).

As indicated above, each bone anchor includes a head portion 16 that is configured to engage a stabilization element, such as the element 25 shown in FIG. 3. The stabilization element can be an elongated rod or a spinal plate. The head portion 16 is configured appropriately for the specific type of stabilization element 25. When the dynamic stabilization construct is complete, load applied to the vertebrae, as indicated by the large arrows in FIG. 3, causes each vertebra $V_1$, $V_2$ to rotate relative to the stabilization element 25, as accommodated by the flexible portions 18. Nominally, movement of one vertebra under external load is isolated from the other vertebra as the flexible portion 18 of the bone anchor 10 bends.

The representation in FIG. 3 illustrates one significant benefit of the present dynamic stabilization system over prior systems. In particular, the center of rotation (CR) for a normal motion segment is represented by the marking $CR_N$. It is believed that an optimum dynamic stabilization system will emulate the normal movement of the motion segment as accurately as possible, given the limited ways in which the system can be fastened to the spine. Consequently, where the dynamic stabilization system permits rotation in the A/P plane, as represented by the center of rotation marking $CR_N$, the more optimum system will exhibit a center of rotation as close to the normal center $CR_N$ as possible. Systems that rely upon providing inter-spinous flexibility,—i.e., those anchored to the transverse process that are connected between adjacent spinous processes via wires or lamina, cables—produce a center of rotation $CR_I$ that is well remote from the normal center of rotation. Systems that rely upon flexibility at the point of fixation to the elongated spinal rod or plate have a center of rotation $CR_F$ that is essentially along the axis of the elongated rod/plate.

However, the present invention offers a center of rotation $CR_R$ that can be is at the surface of the pedicle, and therefor as close as possible to the normal center of rotation as is physically and anatomically possible. The posteriorly positioned centers of rotation $CR_I$, $CR_F$ tend to generate abnormal loading patterns and greater loads on the anterior annulus during normal movements of the spine. The present invention beneficially moves the center of rotation $CR_R$ of the instrumented motion segment anteriorly toward the normal center so that the disc experiences more normal loading patterns during flexion and extension of the spine.

Figure 4B:
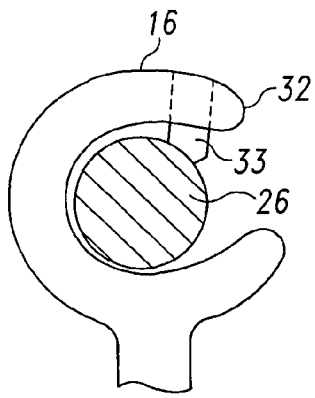

In one embodiment of the invention, the dynamic stabilization system relies upon an elongated rod sized to span a length of the spine between two or more vertebrae. The elongated rod can be configured like a variety of known spinal implants and can include a number of surface finishes, such as smooth polish, knurling or threading. Likewise, a number of engagement mechanisms can be provided for connecting the bone anchor 10 to the stabilization element 25. Thus, the head portion 16 of the anchor may assume a number of configurations, including the configurations shown in FIGS. 4a-4c. The head portion may include an open top connector 30 within which a spinal rod 26 is seated as shown in FIG. 4a. A compression member 31 clamps the rod within the connector 30. Exemplary connectors of this type are described in U.S. Pat. No. 5,545,165 to Biedermann et al. The head portion in FIG. 4b includes a top tightening connector 32 that uses a set screw 33 to clamp the rod 26 within the connector. U.S. Pat. No. 5,282,801 to Sherman is directed to an exemplary top tightening mechanism.

Figure 4C:
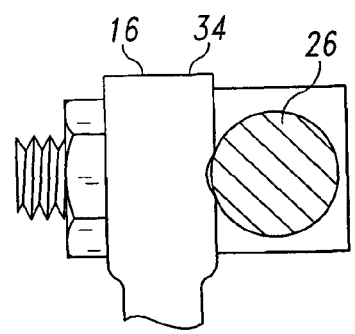

Finally, an eyebolt-type connector 34 may be used as shown in FIG. 4c. Connectors of this type are described in U.S. Pat. No. 5,246,442 to Ashman et al. The specification and figures of each of these patents are incorporated herein by reference. The details of each of these exemplary constructs are known to the person of skill in the field of spinal implants. It should be understood that the connectors shown in FIGS. 4a-4c can be readily used with the anchor 10, as well as other connector configurations adapted to engage an elongated spinal rod.

Figure 5:
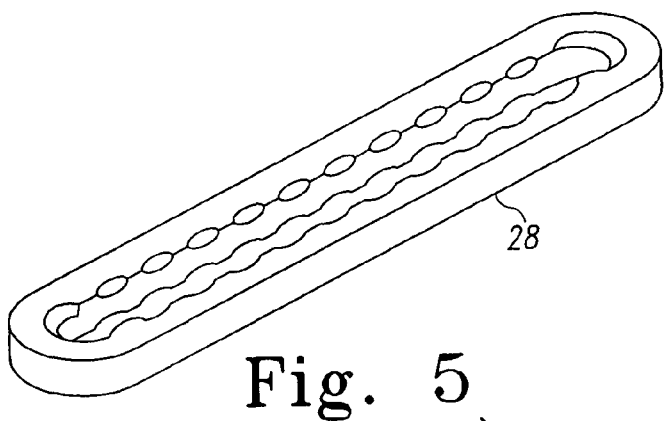
FIG. 5 is a perspective view of a known spinal plate for use with the bone anchor shown in FIG. 1.
Figure 6A:
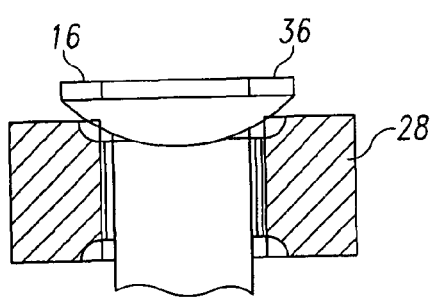
FIGS. 6a-6b are enlarged partial cross-sectional views of alternative head portions for use with the bone anchor shown in FIG. 1, engaged to the spinal plate shown in FIG. 5.
Figure 6B:
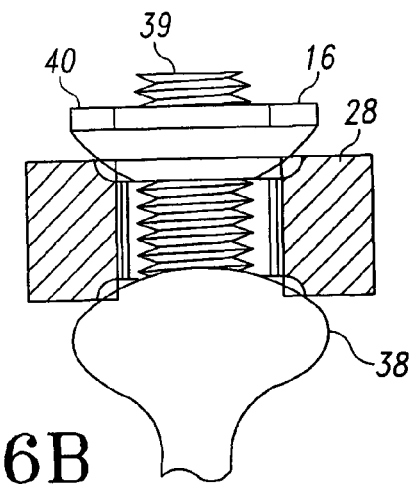

The dynamic stabilization system of the present invention also contemplates implementation using a spinal plate, such as the slotted plate 28 shown in FIG. 5. This plate can be of many known configurations, such as the design described in U.S. Pat. No. 5,209,751 to Farris et al., the disclosure of which is incorporated herein by reference. As shown in FIGS. 6a-6b, the head portion 16 of the bone anchor can assume a number of configurations for engagement with the spinal plate 28. For instance, as shown in FIG. 6a, the head portion may assume a bone screw configuration in which the head 36 of the screw engages the top of the spinal plate 28. In an alternative embodiment, shown in FIG. 6b, the anchor may be in the form of a bone bolt in which an intermediate portion 38 engages the underside of the plate 28. A threaded stem 39 extends through an opening in the plate for engagement with a nut 40. The nut thus sandwiches the plate 28 against the intermediate portion 38. The bone anchor configuration of FIG. 6a and the bone bolt configuration of FIG. 6b are described further in the '751 Patent to Farris et al.

Again, it should be understood that these configurations for the head portion 16 for engagement to a spinal plate 26 are merely exemplary. The principles of the present invention do not depend upon the type of head portion 16 or the type of stabilization element (rod 26 or plate 28) used. Any connection configuration can suffice provided that the function of the flexible portion 18 of the bone anchor 10 is not significantly impeded.

Where the bone engaging portion 12 includes bone threads 14, the bone anchor 10 and/or the head portion 16 must incorporate some feature to allow threading of the anchor into the bone. In the bone anchor configuration 36 of FIG. 6a or the bone bolt configuration 38 of FIG. 6b, the head portion itself includes features for accepting a driving tool, such as a wrench. The feature may include external flats or an internal hex, for instance. External driving flats can be provided on the connectors shown in FIGS. 4a-4c. Alternatively, an internal driving bore may extend through the head portion 16 and into the engagement portion 12, with an appropriately sized Allen wrench used to thread the anchor into the bone.

Figure 7:
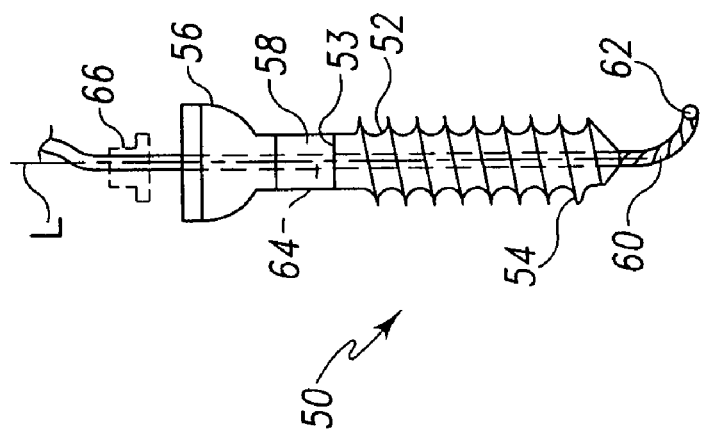
FIG. 7 is an elevational view of a bone anchor in accordance with another embodiment of the present invention. 4

An alternative embodiment of a bone anchor 50 is depicted in FIG. 7. This bone anchor includes a bone engaging portion 52 that can include bone engaging threads 54. Again, as with the anchor 10 discussed above, the bone engaging portion can assume a variety of know configurations adapted for engagement within a spinal motion segment or vertebra. The anchor 50 also includes a head portion 56 that can adopt a number of configurations depending upon the type of stabilization element used for the dynamic stabilization system. For example, the head portion may be configured like the connectors 30, 32, 34, 36 or 38 shown in FIGS. 4a-4c and 6a-6b. For the purposes of illustration, the head portion 56 shown in FIG. 7 is generally in the form of a bone screw, as depicted in FIG. 6a.

In one aspect of this embodiment of the invention, the bone anchor 50 includes a flexible portion 58 interposed between the bone engagement portion 52 and the head portion 56. Unlike the embodiment of FIG. 1, the flexible portion 58 is separate from one or the other, or both, of the engagement portion and the head portion. In other words, in the specific illustrated embodiment the flexible portion 58 is a separate component from the other two portions of the anchor 50. Alternatively, the flexible portion may be integrated into either the engagement portion or the head portion.

Figure 8B:
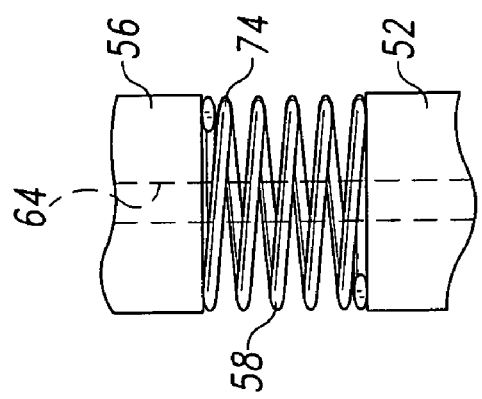
FIGS. 8a-8b are enlarged views of flexible portions for use with the bone anchor shown in FIG. 7.
Figure 8A:
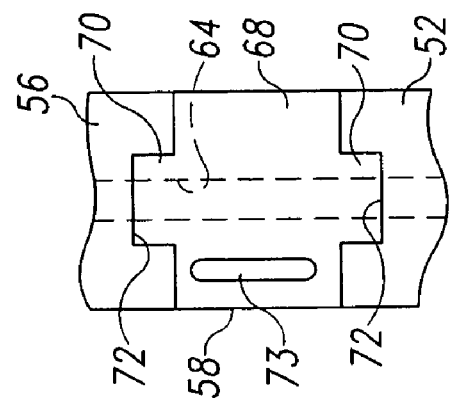

However, in one embodiment, the flexible portion 58 is in the form of a generally cylindrical insert body 68 as shown in FIG. 8a. This insert body 68 is sized and shaped to generally conform to the outer configuration of the engagement portion 52 and/or the head portion 56 to present a substantially smooth transition between these portions. In this embodiment, the insert body 68 is formed of a bio-compatible polymeric or elastomeric material. For instance, the material can be PEEK (polyetheretherketone), polyurethane or similar resilient and flexible materials. Certain bio-compatible "soft" metals, such as Nitinol™ may also be used, taking into account the potential for adverse interaction with the metal of the other portions. The insert body can be formed using conventional techniques for the particular material, such as injection molding.

The choice of material dictates the amount of flexibility for the portion 58. Moreover, the length of the insert body 68 is also a factor in defining the degree of relative motion permitted by the flexible portion 58. It is contemplated that a range of pre-determined insert bodies 68 may be made available to the orthopaedic surgeon, with the bodies calibrated by anticipated range of angular motion. One benefit of the embodiment shown in FIG. 7 is that the bone anchor 50 can be converted into a substantially rigid anchor by replacement of the flexible portion 58 with a substantially rigid spacer having the same size and configuration. Thus, unlike prior arthrodesis systems, the flexibility of each bone anchor used in a dynamic stabilization system can be varied from substantially rigid to very flexible depending upon the patient's pathology and indications. The flexibility of the construct can be established during the implantation surgery by choosing among the range insert bodies. That range of bodies may also include components having varying heights to accommodate differences in vertebral geometry depending upon instrumented vertebral level and patient anatomy.

In one embodiment, the insert body 68 includes interlocking segments 70 that are seated within interlocking notches 72 defined in the engagement portion 52 and head portion 56. The interlocking segments 70 and notches 72 nominally prevent relative rotation between the three components. In addition, the interlocking elements permit torque transmission through the flexible portion 58 when the engagement portion 52 includes bone engaging threads 54. More importantly, the interlocking elements 70, 72 facilitate transmission of bending forces across the flexible portion 58. The interlocking segments 70 also help keep the construct together under bending loads and act as a fulcrum when load is applied to the engagement portion 52. It is understood that the engagement portion 52 can be engaged to the vertebral bone prior to introduction of the insert body 68.

In an alternative embodiment, shown in FIG. 8b, the flexible portion 58 is in the form of a spring element 74. In the illustrated embodiment, the spring element 74 is a coil spring that is interposed between the lower engagement portion 52 and the upper head portion 56. Preferably, the spring element 74 is affixed to these lower and upper portions in a suitable manner, such as by welding or mechanical fastening. As with the insert body 68, the flexibility of the spring element 74 can be determined by spring material and dimensions. Preferably, the spring element 74 is formed of a bio-compatible and fatigue-resistant metal, such as stainless steel. The wire diameter and coil dimensions may be adjusted to modify the anticipated flexibility of the flexible portion 58. Preferably, the outer dimension of the spring element 74 is sized to provide a uniform transition from the adjoining portions 52 and 56 to the flexible portion 58. Most preferably, the spring element 74 is surrounded by a sheath to prevent bone ingrowth into the spring element.

Both embodiments of the flexible portion 58 shown in FIGS. 8a-8b permit relative movement between the engagement portion 52 and head portion 56 in radial-longitudinal planes transverse to the longitudinal axis L of the anchor 50. Unlike the anchor 10 of the previous embodiment in which the relative movement is limited to a single transverse plane, the movement permitted by the flexible portion 58 in the embodiment of FIG. 7 permits movement in all radial-longitudinal planes about the longitudinal axis L.

This range of flexible motion can be modified on the embodiment of FIG. 8a by introducing stiffening elements 73 to the insert body. These stiffening elements may be integrally formed with the body itself, such as an injection molded feature in a polymer body. Alternatively, the stiffening elements may be a separate component, such as a metal strip, that is attached to or formed within the insert body 73. Adding stiffening elements 73 within certain radial-longitudinal planes can limit or prevent bending in that plane, relative to other radial-longitudinal planes without the stiffening elements. In lieu of stiffening elements, it is contemplated that the insert body 68 can present a non-cylindrical form and even a non-uniform cross-section to adjust bending properties in different radial-longitudinal planes.

Returning to FIG. 7, a further aspect of the present embodiment is depicted in which a tensioning element 60 is associated with the bone anchor 50. In the specific embodiment, the tensioning element 60 is a cable that extends through a cable bore 64 defined through each of the portions of the bone anchor. The cable 60 terminates at its distal end in a retention member 62 that is configured to prevent its passage through the bore 64. In a specific embodiment, the retention member is in the form of an enlarged head or a ball that bears against the distal tip of the engagement portion 52. Alternatively, the retention member and engagement portion can be configured so that the retention member is buried within the bone anchor 50.

As shown in FIG. 7, the tensioning cable 60 extends through each of the engagement portion 52, flexible portion 58 and head portion 56, exiting the anchor at the proximal end of the head portion. The cable 60 is used to pull the three components together and hold them in compression. Consequently, a cable fixation feature 66 is provided that maintains the cable in tension and the bone anchor components in compression. In a preferred embodiment, the cable fixation feature is a crimp that is crimped around the cable and that bears against the proximal face of the head portion 56. One type of crimp suitable for the present invention, known as a top-hat crimp, is shown and described in U.S. Pat. No. 5,312,410 to Miller et al. The '410, the disclosure of which is incorporated herein by reference, also describes a tensioning apparatus that can be used to draw the cable 60 into tension.

Other forms of cable fixation feature other than the crimp 66 are contemplated by the present invention. The selection of fixation feature is generally contingent on the type of stabilization member 25 to which the bone anchor 50 is engaged. The bone anchor configuration shown in FIG. 7 is particularly suited for use with a spinal plate, such as the plate 28 shown in FIG. 5. A bone bolt configuration, such as the anchor 78 shown in FIG. 9 can also implement the flexible portion 58 and tensioning cable 60 just described. The anchor 78 is similar to the bone bolt configuration 38 shown in FIG. 6b.

Figure 9:
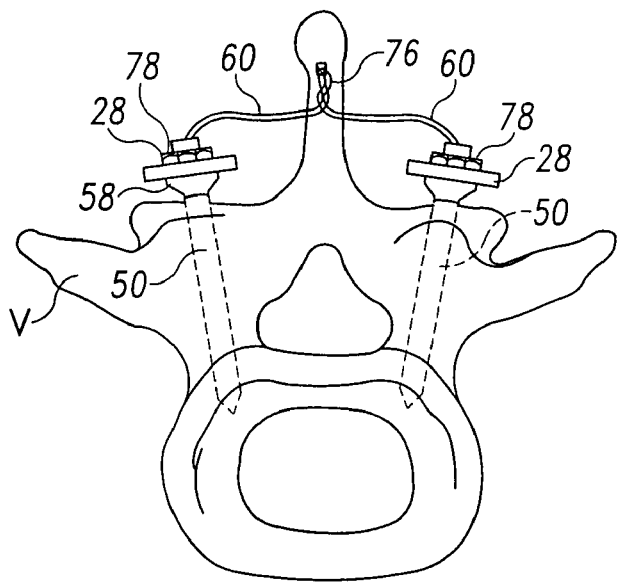
FIG. 9 is a view of a vertebra instrumented with bone anchors as shown in FIG. 8 and a spinal plate as shown in FIG. 5.

A stabilization system is shown in FIG. 9 that utilizes two spinal plates 28 adjacent each pedicle of the vertebra V. A bone anchor 50 is anchored in each pedicle and is engaged to a corresponding spinal plate 28. A crimp, such as the crimp fixation feature 66 shown in FIG. 7, is used to complete the compression assembly of each bone anchor 50. Alternatively, as depicted in FIG. 9, the two cables 60 from the two anchors 50 can be fastened together, such as by a cable twist 76. Alternatively, an interlocking configuration using a cable loop and top-hat crimp can be utilized, in a manner similar to that depicted in the '410 Patent discussed above.

Other cable arrangements may be used with the present invention. For instance, the cable 60 can be wrapped and fastened around a spinal rod, such as the rod 26 described above. For instance, the tensioning element 60 may include two cable portions extending upward through the cable bore 64. The ends of the cable portions can be twisted or crimped together around a spinal, in the manner shown in U.S. Pat. No. 5,242,446 to Steffee et al., the disclosure of which is incorporated herein by reference. With this type of cable arrangement, the head portion 56 may be modified to engage a spinal rod while also accommodating the twisted cable portions. Another exemplary cable arrangement for use with a spinal rod is shown in U.S. Pat. No. 6,514,255 to Ferree, the disclosure of which is incorporated by reference.

In one aspect of the invention, the amount of flexibility accommodated by the flexible portion 58 may be modified by the amount of tension in the tensioning element 60, or more particularly, the amount of compression between the components of the anchor 50. In order to maintain the proper compression over the life of the stabilization implant, it is desirable that the cable be formed of a material that is not susceptible to stretching or loosening over time. Thus, in a preferred embodiment, the cable is formed of wound filament strands that are pre-stretched. The filaments can be formed from a variety of biocompatible materials, such as stainless steel or some form of polyester.

When the engagement portion 52 of the bone anchor 50 includes threads 54, the bone anchor must provide some means for driving the anchor into bone. As explained above in connection with the bone anchor 10, the head portion 56 can be configured for engagement with a known driving tool. However, the interposition of the flexible portion 58 can limit the ability to transmit torque between the head portion 56 and the bone engaging portion 52. Where the flexible portion includes the insert body 68 and interlocking elements 70, 72, torque can be transmitted across the insert body.

In an alternative embodiment, the engagement portion 52 is provided with an internal driving feature at its proximal face 53. Thus, the proximal face defines a hex recess to receive a hex driving tool. The tool can be used to drive the engagement portion 52 into the bone so that the proximal face 53 is generally flush with the bone surface. Some modification to a standard hex driving tool may be necessary to accept the tensioning cable 60 that extends upward through the cable bore 64. Once the engagement portion 52 is within the vertebra, the flexible portion 58 and head portion 56 can be successively threaded onto the cable 60 and the cable tensioned and fixed to complete the assembly.

The tension element 60 can also take on the form of a flexible rod having a threaded proximal end that projects outside the head portion 56 when the construct is assembled. A nut is threaded down onto the threaded end of the flexible rod to draw the retention member 62 upward and to compress the portions of the bone anchor 50. The proximal end of the flexible rod can be enlarged to increase the diameter of the threaded end for greater holding power.

Figure 10:
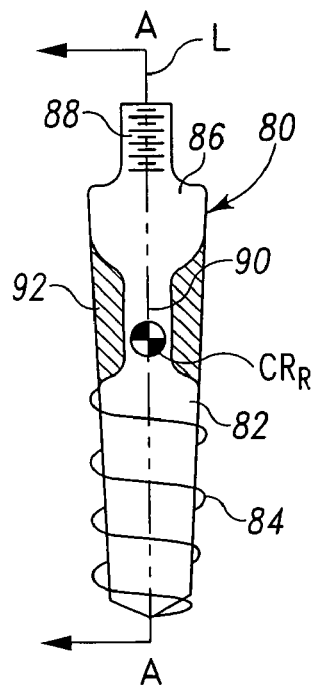
FIG. 10 is an elevational view of a bone anchor in accordance with a further embodiment of the invention.

A further embodiment of the invention resides in a bone anchor 80 shown in FIG. 10. This anchor includes an engagement portion 82 which, like the anchors 10 and 50 above, includes threads 82 or any other configuration suitable for engagement to the spine or a spinal motion segment. The anchor 80 also includes a head portion 86, which includes a threaded post 88 as part of a bone bolt configuration similar to that shown in FIG. 6b. Again, like the prior embodiments the head portion 86 can take on a number of configurations depending upon the nature of the stabilization element.

Figure 11:
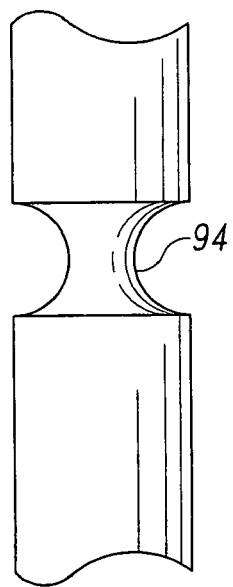
FIG. 11 is an enlarged view of an alternative flexible portion for the bone anchor shown in FIG. 10.

In accordance with one feature of this embodiment, the anchor 80 is provided with a flexible portion 90 that has a reduced cross-section relative to at least the bone engagement portion 82. Where the bone anchor is a cylindrical anchor, such as a bone bolt, the flexible portion 90 can have a diameter less than the diameter of the engagement portion. The reduced diameter of the flexible portion determines the amount of flexibility of the portion 90. In addition, the overall dimension of the flexible portion affects the flexibility. For instance, in the specific embodiment shown in FIG. 10, the flexible portion 90 is elongated. In an alternative embodiment, the flexible portion can have a much more limited axial dimension, such as the circumferential groove configuration 94 shown in FIG. 11.

As with the bone anchor 50, the flexible portion 90 can permit bending movement in all radial-longitudinal planes transverse to the longitudinal axis L. Alternatively, the flexible portion 90 has a modified cross-section—i.e., a cross-section that does not necessarily parallel the shape of the cross-section of the engagement portion 82. The cross-section of the flexible portion may be altered to control the degree of stiffness in different radial-longitudinal planes. For instance, the flexible portion can be generally elliptical so that the width or thickness in one direction is equal to the width or diameter of the engagement portion in that direction, but the width perpendicular to that direction is less than the engagement portion diameter.

In this preferred embodiment, a sleeve 92 surrounds the flexible portion 90. The sleeve is intended to prevent bone ingrowth into the reduced cross-section of the flexible portion. In specific embodiment, the sleeve 92 is formed by a polymer molded into the space surrounding the reduced cross-section portion. The surface of the molded sleeve may be tailored to conform to the outer profile of the anchor 80. Alternatively, the sleeve may be a flexible washer that is pushed over the exposed head portion and flexible portion of the anchor when it is initially engaged to the motion segment. The sleeve 92 must be flexible enough so that its presence is generally transparent to the bending capabilities of the flexible portion 90. As a further alternative, the sleeve 92 can be configured to add stiffness to the flexible portion 90 of the bone anchor. With this alternative, a common bone anchor design can be used for most dynamic stabilization constructs, with only the sleeve being changed depending upon the desired flexibility.

As mentioned above, fatigue resistance is an important characteristic for the bone anchor 80. The strength of the anchor can be enhanced by the material, design and manufacturing approaches noted above. With the bone anchor 80 the flexion point falls within the reduced diameter portion 90. The reduced diameter in this region can be expected to be more susceptible to fatigue than the remainder of the anchor. As discussed above, material selection for the anchor may impart sufficient fatigue resistance to the reduced diameter portion 90.

Alternatively, the geometry of the reduced diameter portion may be altered to increase the fatigue limit of that portion of the anchor. In one alternative embodiment, the bone anchor 80 shown in FIG. 10 can be modified in its transverse cross-section (i.e., the cross-section taken along line A-A of FIG. 10 as viewed in the direction of the arrows). In particular, a modified bone anchor 80' includes a shank 82', head portion 86' and threaded post 88' similar to the like components of the anchor 80. Furthermore, the intermediate flexible portion 90' has the same reduced profile as the portion 90 as viewed in FIG. 10. However, in this alternative embodiment, the portion 90' has an increased dimension transverse to the reduced dimension. The portion 90' is thinner in the plane that defines the flexion point $CR_R$ for the anchor (i.e., the plane depicted in FIG. 10) and thicker in the transverse plane (i.e., the plane depicted in FIG. 12). The width or thickness of the portion 90' in the transverse plane can be increased in proportion to the decrease in thickness in the flexion plane, so that the portion exhibits a width that extends outside the diameter of the shank 82' or of the head portion 86'. Since the flexible portion 90' is situated outside the pedicle of the vertebra, it is not driven into the bone so the portion can assume a larger non-cylindrical dimension. This provides a secondary benefit of preventing inadvertent countersinking of the flexible portion within the pedicle during insertion.

Another embodiment of the invention resides in a bone anchor as shown in FIGS. 13-15. The bone anchor 100 includes a bone engaging portion 102, a head portion 104 and an intermediate flexible portion 106. The head portion can be configured as shown in U.S. Pat. No. 5,261,912 to Frigg, the disclosure of which is incorporated herein by reference. In particular, the head portion 104 defines a rod receiving channel 108 for top loading of a spinal rod, such as the rod 26. The base of the channel can include includes features 110 for holding the rod against translation. The channel 108 includes internal threads 112 that are configured to engage a clamping member 120 shown in FIG. 15. The clamping member 120 includes an externally threaded boss 122 that engages the internal threads 112 of the channel 108. The boss 122 defines a surface 123 that bears against the rod within the channel 108 to clamp the rod against the holding features 110. The clamping member 120 also includes an outer cap 124 that fits around the outside of the head portion 104 to close the clamp and to prevent outward flaring of the head portion when the clamping member is tightened onto the head portion. The clamping member 120 can include an internal feature 126 to engage a driving tool.

Returning to FIGS. 13 and 14, the bone anchor 110 includes an intermediate flexible portion 106 that serves the same function as the flexible portions described above. In this embodiment, the flexible portion includes a slot 106 that originates at the head portion 104 and extends longitudinally along the axis L of the anchor toward the engagement portion 102 of the anchor. The slot 107 is oriented perpendicular to the channel 108 so that the anchor provides flexibility in the plane that includes the rod 26 and the bone anchor 100. As with the above described bone anchors of the present invention, the bone anchor 100 is engaged within a vertebra, and particularly the pedicle of the vertebra, with the flexible portion 106 outside the bone.

It is understood that the bone anchor 100 can include a head portion 104 configured to engage a spinal rod in a different manner, or to engage an elongated plate spanning a portion of the spine. For instance, any of the alternative configurations shown in FIGS. 4a-4c can be adapted to the bone anchor 100. Moreover, the slot 107 may be modified to define a closed slot within the intermediate flexible portion 106 only. In other words, rather than originating at the top of the head portion, as shown in FIG. 14, the slot 107 can originate near, and preferably below, the base of the rod channel as represented by the dashed line 109 in FIG. 14.

With each of the embodiments of the present invention it is contemplated that each motion segment can be instrumented with a bone anchor having a flexibility tailored to that particular level. For instance, where the dynamic stabilization construct spans several vertebrae, only some of the motion segments may be amenable to use of the dynamic or soft stabilization. Some motion segments may require rigid stabilization, in which case a known rigid bone anchor can be employed if appropriate. Different flexibilities may be incorporated into bone anchors along the length of the spine, and even on opposite sides of the sagittal plane, bearing in mind that a principal goal of the construct is to restore normal loading patterns for the spine.

Certain embodiments of the invention are also well-suited to revision surgeries, where changes to the construct may be necessary months and even years after the initial implantation. Since the preferred construct maintains the flexible portion outside the vertebral bone, it can be accessible in a revision surgery to replace the flexible portion 58 of the bone anchor 50, for instance.

The dynamic stabilization system of the present invention is well suited as an adjunct to a disc repair procedure. For instance, the intervertebral disc D (see FIG. 3) may require augmentation or replacement, depending upon the severity of the damage or disease to the disc. Where the disc is intact, it is important to maintain the loading pattern as normal as possible since this loading pattern helps hydrate the disc D and flush toxins from the disc.

Devices have been developed for replacement of the intervertebral disc. In some cases, the device is a mechanical device that is configured to mimic the mechanics of the disc motion. In more recent years, the nucleus pulposus of the intervertebral disc has been replaced with a polymer prosthesis that emulates the physical and chemical properties of the disc. In particular, these types of prostheses are intended to preserve or restore the movement and load response of the affected disc as close to the natural disc as possible. One such material is a hydrogel that has similar elastic properties to the natural nucleus pulposus and that shares a similar fluid transport mechanism to the natural disc. This material can be used to replace the entire nucleus pulposus, or to augment the existing nucleus where voids or other defects in the nucleus exist.

Even where the intervertebral disc has been replaced with a mechanical device, or where all or part of the nucleus pulposus has been replaced with a polymer prosthesis, restoration and maintenance of normal spinal segment motion is important. Consequently, it is contemplated that the dynamic stabilization system of the present invention, including bone anchors such as the anchors 10, 50, 80 and 100, can be used in connection with disc/nucleus repair or replacement procedures.

Prior dynamic stabilization systems rely upon flexible elements spanning between transverse processes or laminae. One significant drawback of these types of systems is that they cannot be used for all types of spinal surgical procedures. For instance, in one procedure for the correction of scoliosis, a spinal rod, such as the rod 26 shown in FIGS. 16a-b, is bent to a contour C and engaged to each vertebra of the deformed spinal column. The rod 26 is then rotated about its axis in the direction R shown in FIG. 16a to de-rotate the spine. The resulting spine assumes the more normal configuration and curvature shown in FIG. 17a-b in which the lateral curvature has been corrected (FIG. 17a) and the normal lordosis and kyphosis has been restored to the spine in the A/P plane (FIG. 17b). In many cases, a second rod 26 can be added to the contra-lateral side of the spine to stabilize the construct.

The above mentioned prior dynamic stabilization systems cannot accomplish correction of scoliosis through rod de-rotation because they lack the force-transmission interface with the rotated rod. These prior systems are also unable to maintain a fixed relationship between adjacent vertebrae because the flexible segments span the vertebrae. On the other hand, the bone anchors 10, 50, 80 and 100 of the present invention are well-suited to this type of procedure because the anchors can be engaged to a spinal rod for the necessary force transmission. Moreover, the bone anchors of the present invention allow for different degrees of flexibility at each instrumented vertebral level. For instance, as depicted in FIG. 16a, the two vertebrae at the superior and inferior ends of the construct may incorporate the flexible bone anchors of the present invention, while the intermediate vertebrae can be instrumented with known rigid fasteners (and in some cases can be fused). Adding dynamic flexibility at the distal ends of long constructs, such as the construct depicted for correction of scoliosis, is believed to reduce the occurrence of "transition syndrome", a condition manifested by accelerated degeneration of the distal vertebrae. due to abnormal loading at distal segments in a rigid construct. The stress concentration present at the interface between the rigid fusion and the flexible natural segments is believed to accelerate the degeneration process. By adding flexible segments, with the ability to vary the stiffness of the segments as described above, the distribution of stress along the spine can be made more uniform.

The present invention offers a similar benefit to a reduction procedure, such as for correction of spondylolisthesis, as depicted in FIG. 18. Where a severe slip has occurred, such the slip of the $L_5$ vertebra shown in FIG. 18, one approach has been to pull the slipped vertebra up to a rigid stabilization member, such as the rod 26. In this case, a bone anchor 130 is engaged to the flanking spinal elements, such as the $L_4$ vertebra and the sacrum S. Preferably, the anchor engaging the sacrum is a rigid fastener, while the anchors engaging one or both of the vertebrae can be one the bone anchors of the present invention. Since the bone anchors 10, 50, 80 and 100 allow force transmission through the anchor, the anchor engaged to the $L_5$ vertebra is pulled toward the rod 26 to reduce the slip at that vertebra. Again, the prior dynamic stabilization systems cannot accomplish this type of reduction.

For the purposes of promoting an understanding of the principles of the invention, reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

What is claimed is:

1. A method for dynamic stabilization of motion segments of the spine comprising the steps of:
  repairing or replacing all or part of the intervertebral disc between at least two vertebrae;
  positioning a stabilization element adjacent the spine, the stabilization element configured to span a length of the spine between the at least two vertebrae;
  engaging bone anchors to at least two vertebrae, each bone anchor including an engagement portion configured for engagement within a vertebra, a head portion configured for engagement to said stabilization element outside the vertebra, and a flexible portion between said engagement portion and said head portion; and
  coupling the bone anchors to the stabilization element outside the vertebrae, with each of the bone anchors coupled to permit deflection of the bone anchor between the stabilization element and the corresponding vertebra to which such bone anchor is engaged.

2. The method for dynamic stabilization according to claim 1, wherein the step of repairing or replacing includes replacing all or part of the nucleus pulposus with a polymeric prosthesis having physical properties substantially similar to the physical properties of a natural nucleus pulposus.

3. A method for dynamic stabilization of a motion segment of the spine comprising the steps of:
  providing a dynamic stabilization system including a stabilization element configured to span a length of the spine between at least two vertebrae and at least two anchors each of said anchors including a head portion configured for contacting said stabilization element and an engagement portion configured for engaging a vertebra, each of said anchors including a flexible portion between said head portion and said engagement portion configured to permit relative movement between said head portion and said engagement portion;

introducing a device into an intervertebral space between two vertebrae to at least partially maintain or restore the natural motion of the disc at the motion segment; and coupling said dynamic stabilization system across the motion segment, whereby the bone anchor engaged in each of the two vertebrae permits natural motion of the motion segment by deforming a portion of the bone anchor.

4. The method for dynamic stabilization according to claim 3, wherein the device includes a device for replacing or augmenting the nucleus pulposus of the intervertebral disc.

5. The method for dynamic stabilization according to claim 4, wherein the step of introducing a device includes introducing a polymeric prosthesis to replace or augment the nucleus pulposus in which the polymeric prosthesis exhibits physical properties similar to the natural nucleus pulposus.

6. The method for dynamic stabilization according to claim 5, wherein the polymeric prosthesis is formed from a hydrogel.

7. The method for dynamic stabilization according to claim 4, wherein the device for replacing or augmenting the nucleus pulposus is a mechanical device.

8. A method for dynamic stabilization of a motion segment of the spine comprising the steps of:

introducing a device into an intervertebral space to at least partially maintain or restore the natural motion of the disc at the motion segment; and coupling a dynamic stabilization system across the motion segment that permits substantially normal loading patterns on the disc by emulating substantially normal movement of the motion segment in the anterior/posterior (A/P) plane in both directions during normal flexion and extension, said coupling step includes providing a stabilization element configured to span a length of the spine between at least two vertebrae and a bone engaging anchor for each vertebra, each of said anchors includes a head portion configured for contacting the stabilization element and an engagement portion configured for engaging a vertebra, at least one of said anchors being configured to provide a center of rotation situated between the stabilization element and the normal anatomic center of rotation for the motion segment.

9. The method for dynamic stabilization according to claim 8, wherein the step of introducing a device includes introducing a device for replacing or augmenting the nucleus pulposus of the intervertebral disc.

10. The method for dynamic stabilization according to claim 9, wherein the step of introducing a device includes introducing a polymeric prosthesis which exhibits physical properties similar to the natural nucleus pulposus.

11. The method for dynamic stabilization according to claim 10, wherein the polymeric prosthesis is formed of a hydrogel.

12. The method for dynamic stabilization according to claim 8, wherein the center of rotation of the motion segment is located substantially at the posterior surface of the pedicle of the vertebrae of such segment.

* * * * *